(12) United States Patent
Brånemark (10) Patent No.: US 6,319,000 B1
(45) Date of Patent: Nov. 20, 2001

(54) DENTAL PROSTHESIS SYSTEM, COMPONENTS FOR DENTAL PROSTHESIS SYSTEM AND METHODS FOR SUCH A DENTAL PROSTHESIS SYSTEM

(75) Inventor: Per-Ingvar Brånemark, Mölndal (SE)

(73) Assignee: Medevelop AB, Gothenburg (SE)

( * ) Notice: Subject to any disclaimer, the term of this patent is extended or adjusted under 35 U.S.C. 154(b) by 0 days.

(21) Appl. No.: 09/202,988

(22) PCT Filed: Jun. 12, 1997

(86) PCT No.: PCT/SE97/01036

§ 371 Date: Mar. 2, 1999

§ 102(e) Date: Mar. 2, 1999

(87) PCT Pub. No.: WO97/49351

PCT Pub. Date: Dec. 31, 1997

(30) Foreign Application Priority Data

Jun. 27, 1996 (SE) .................................................. 9602554

(51) Int. Cl.[7] ............................................................ A61C 8/00
(52) U.S. Cl. ................................................ 433/75; 433/173
(58) Field of Search .................................. 433/173, 75, 76, 433/174

(56) References Cited

U.S. PATENT DOCUMENTS

| | | | |
|---|---|---|---|
| 3,508,334 | * | 4/1970 | Weissman . |
| 4,325,373 | * | 4/1982 | Slivenko et al. . |
| 4,906,191 | * | 3/1990 | Söderberg ........................... 433/173 |
| 4,931,616 | * | 6/1990 | Sillard ................................. 433/433 |
| 4,968,250 | * | 11/1990 | Small . |
| 4,998,881 | * | 3/1991 | Lauks . |
| 5,098,296 | * | 3/1992 | Cullen . |
| 5,133,660 | * | 7/1992 | Fenick . |
| 5,215,460 | * | 6/1993 | Perry ..................................... 433/75 |
| 5,302,122 | * | 4/1994 | Milne .................................. 433/173 |
| 5,556,278 | * | 9/1996 | Meitner ................................. 433/75 |
| 5,613,852 | * | 3/1997 | Bavitz . |
| 5,636,986 | * | 6/1997 | Pezeshkian . |
| 5,718,579 | * | 2/1998 | Kennedy . |
| 5,741,133 | * | 4/1998 | Gordils et al. ......................... 433/76 |
| 5,842,859 | * | 12/1998 | Palacci ................................. 433/75 |

FOREIGN PATENT DOCUMENTS

| | | |
|---|---|---|
| 0210967 | 2/1987 | (EP) . |
| 0622053 | 11/1994 | (EP) . |
| 8502337 | 6/1985 | (WO) . |
| 9100711 | 1/1991 | (WO) . |

* cited by examiner

Primary Examiner—Ralph A. Lewis
(74) Attorney, Agent, or Firm—Ostrolenk, Faber, Gerb & Soffen, LLP

(57) ABSTRACT

The invention relates to a dental prosthesis system incorporating a superstructure (4, 5), a positioning device, and fixtures (1) that are implantable in a person's jawbone. Each fixture (1) is anchored in the jawbone and its opposite end is arranged so that it will be possible to attach a superstructure (4, 5) to it. By means of the positioning device, fixtures (1) are implanted at definite positions and in definite directions, usually parallel directions. The superstructure includes prefabricated elements with fastening devices (8, 9) that can be attached to fixtures (1). In accordance with the invention, reference device (1a) is designed to put the positioning device in place in such a way as to reliably provide the aforesaid definite positions and directions, therewith facilitating the use of prefabricated superstructures. Through its other aspects, the invention relates to significant components suitable for a dental prosthesis system of this type. Moreover, the invention relates to methods used in connection with the application of the dental prosthesis system.

18 Claims, 5 Drawing Sheets

DENTAL PROSTHESIS SYSTEM, COMPONENTS FOR DENTAL PROSTHESIS SYSTEM AND METHODS FOR SUCH A DENTAL PROSTHESIS SYSTEM

The present invention relates, in its first aspect, to a dental prosthesis system of the type set forth in the preamble to claim 1. Other aspects of the invention relate to a positioning device of the type set forth in the preamble to claim 21, to a drill-guiding insert of the type set forth in the preamble to claim 27, to a set of such drill-guiding inserts of the type set forth in the preamble to claim 30, to a fixture-guiding insert of the type set forth in the preamble to claim 31, to a fixture-aligning device of the type set forth in the preamble to claim 32 and to a superstructure of the type set forth in the preamble to claim 34. All of these other aspects of the invention are related to components intended for use with a dental prosthesis system in accordance with the invention's first aspect. The invention relates, in addition, to a method of attaching a superstructure to fixtures of the type set forth in the preamble to claim 39, to a method for aligning a drilling device for making fixture holes of the type set forth in the preamble to claim 40 and to a method for emplacing a superstructure of the type set forth in the preamble to claim 45.

It is known to implant fixtures in the jawbone of a toothless person. To make certain the fixtures are anchored permanently, a number of factors must be fulfilled with regard to, among other things, material selections and operation techniques. In practice, fixtures developed by Professor Branemark made of pure titanium with a micro-pitted surface have displayed very good long-term anchoring properties. The screw-shaped fixtures are operated into the jawbone where they are allowed to heal in—osseointegrate—throughout a certain time period, usually a few months. Teeth can thereafter be mounted in the fixtures, Most types of these implanted elements are provided with external threads—and are thus implanted screws—and they are attached by screwing them into holes made in the bone tissue. The holes are usually pre-threaded, but it is also possible to screw in self-tapping screws. Implanted elements normally require shorter or longer times for healing-in before they should be exposed to significant loads. On implanted elements, one can attach individual teeth, i.e. one tooth per element, but a number of implanted elements, at least two, can also serve as attachment points for a bridge structure containing several teeth or even a complete row of teeth. For this purpose, a suitable design for the free end of an implanted element could comprise, for example, internal threads in a cylindrical bore in a tooth element that engage external threads on the cylindrical attachment part of a single-tooth prosthesis.

A simple bridge structure intended for attachment to at least two implanted elements is known through SE-448 599 (patent application No. 8503580-6). The bridge structure incorporates an essentially rigid bridge base which is attached directly to the titanium elements by means of screws and mounting devices for removable attachment of a row of teeth on the bridge base. The advantages of a rigid bridge base include the fact that the row of teeth can be attached in a simple manner and that the bridge base is easy to produce. This known device is, however, disadvantageous because the spacer elements must be attached in the jawbone with precise parallelism and with their free ends in a pre-determined plane and spaced a pre-determined distance apart so that it will be possible to mount the bridge base without strain, instead of requiring individual adaptation in advance to the positions of the spacer element's free ends.

If this degree of accuracy cannot be achieved, which is probably the normal case, it is necessary to individually adapt the bridge base to the spacer elements. This adaptation is facilitated, as set forth for example in Swedish published specification No. 446 370, by a pillar-shaped spacer element that is mounted between each implanted element and the bridge structure. Both ends of the spacer element are conically tapered. The free end has a threaded bore so that it can be screwed into a mating hole in a dental prosthesis. Between the dental prosthesis and the conically-shaped free end part there is an arrangement consisting of a sleeve-shaped part having conical internal and external shell-surfaces. Even though this known device has a certain flexibility, the aforesaid specification calls for an impression of the pillar element positions, and possible necessary adjustment of the fit between the conical surfaces of the bridge and the sleeve-shaped parts before final mounting can take place.

To some extent, these disadvantages are avoided by a device that affixes dental bridges in accordance with Swedish patent application No. 8800082-3. Here, the spacer elements have cone-shaped free ends, and the bearing bridge structure incorporates sleeves designed with conical bores that are used to mount the conical ends of the spacer elements, wherewith each sleeve has two lateral vanes. The adjoining vanes on adjacent sleeves overlap each other, and they are joined by means of screws. However, the design/construction of this device is not optimal with regard to, among other things, hygiene, strength and mounting simplicity for a row of teeth.

The mounting of dental bridges requires a great deal of work, and as a result the costs of reconstructing a complete upper or lower jaw are relatively high. Moreover, reconstruction is very time-consuming, even for the patient. It is therefor desirable to reduce, by means of user-friendly implanting and mounting solutions, the amount of time and work needed for full-jaw reconstructions—including reconstructions that only involve a significant contiguous part of a row of teeth.

Through SE-501 174, a dental prosthesis system is known in which a dental bridge is attached with fixtures via fitting agents arranged between each fixture and the dental bridge's fastening devices. The fitting agents fit precisely the individual fixture's spacer elements and they also fit, but with a certain amount of clearance, the respective fastening devices on the dental bridge. The bridge can be affixed to the fitting agents by means of adhesive or hardening layers applied in the clearances, and the fitting agents are removably attachable to the respective spacer elements.

Through SE-500 851 a dental prosthesis system is also known in which a bridge base is fastened to fixtures attached in a person's jawbone. The fixtures are attached in the jawbone in four holes that are drilled using a jig. The bridge base can be supplied as a prefabricated element selected from an existing assortment of bridge bases.

When using dental bridges that require little or no processing in order to be adapted to the fixtures implanted in a person's jawbone, a technique has thus been used which is based on introducing adjustment or adaptation provisions for the bridge's attachment and also a technique in which a drilling jig is used in an attempt to achieve the necessary precision. This latter alternative imposes stringent requirements regarding how such a drilling jig or other positioning device is applied and handled when holes for the fixture are being drilled.

Against this background, the purpose of the present invention is to provide a dental prosthesis system and components for such a dental prosthesis system that will permit the use of prefabricated superstructures with minimized risk of misfits, thereby minimizing the need for individual adaptation of the superstructure when it is attached to the patient.

In accordance with the invention, this has been achieved through a dental prosthesis system of the type set forth in the preamble to claim 1 which displays the special properties set forth in the characterizing clause of this claim, through the use of a positioning device in accordance with the preamble to claim 21, a drill-guiding insert in accordance with the preamble to claim 27, a fixture-guiding insert in accordance with the preamble to claim 31, a fixture-aligning device in accordance with the preamble to claim 32 and a superstructure in accordance with the preamble to claim 39, all of which display the special properties set forth in the characterizing clauses of the respective claims, and through a set of drill-guiding inserts in accordance with claim 30.

Moreover, this has been achieved by means of a method of the type set forth in the preamble to claim 39 which includes the special measures set forth in the characterizing clause of this claim, through a method of the type set forth in the preamble to claim 40 which includes the special measures set forth in the characterizing clause of this claim, and through a method of the type set forth in the preamble to claim 45 which includes the special measures set forth in the characterizing clause of this claim.

Thanks to the fact that the dental prosthesis system includes a reference device related to the patient's jawbone that is used as the positioning device, it is possible for the positioning device to position and orient very precisely the fixtures used for attachment. This makes it easier to match them, with minimized risk of error, to a superstructure having prefabricated fastening devices. Because of this, the need for subsequent adjustment of the prefabricated element will be eliminated or at least less than what has been required with the techniques used heretofore. This not only reduces the costs of anchoring a dental prosthesis but leads to reduced discomfort and trouble for the patient due to the fact that the necessary treatment time is relatively short. Through the invented system and its components it becomes possible to use a single-visit method to emplace the superstructure. One thus need not wait the 3–6 weeks normally required for the fixtures to osseointegrate in order to acquire, among other things, the torsional resistance needed to withstand a significant load. The superstructure can thus be emplaced earlier and it will, in fact, be possible to do this immediately after the fixtures are anchored.

In a preferred embodiment of the invention, the reference device comprises the first of the prosthesis fixtures anchored in the jawbone. Since it is then used to guide the positioning device into place, optimal precision is ensured for the relative positioning and orientation of the other fixtures.

In another preferred embodiment, the positioning device comprises a drilling jig. Using this, after it has been aligned by means of the reference device, holes for the fixtures can be made at well-defined positions so that the superstructure, which is subsequently attached very precisely to the fixtures, will have the prefabricated fastening elements positioned in such a way that they fit the anchored fixtures.

The superstructure can be suitably arranged as a separate bar provided with fastening devices and with a dental prosthesis bridge that can be attached to the bar. In an alternate preferred embodiment of the invention, the fastening devices are arranged directly on the dental prosthesis bridge.

In yet another preferred embodiment of the invention, a deformation device is provided between the supporting surface on the fixture and a bearing surface on a corresponding attachment unit. If, in spite of the precision obtained, a certain alignment deviation and/or height deviation should occur for any of the fixtures, it can be absorbed by the deformation device.

The aforesaid and other advantageous embodiments of the dental prosthesis system, positioning device and superstructure are set forth in the dependent claims.

The invention is explained in greater detail in the detailed description that follows of the preferred embodiments of the invention, with reference to the attached drawings, where.

Figure 1:
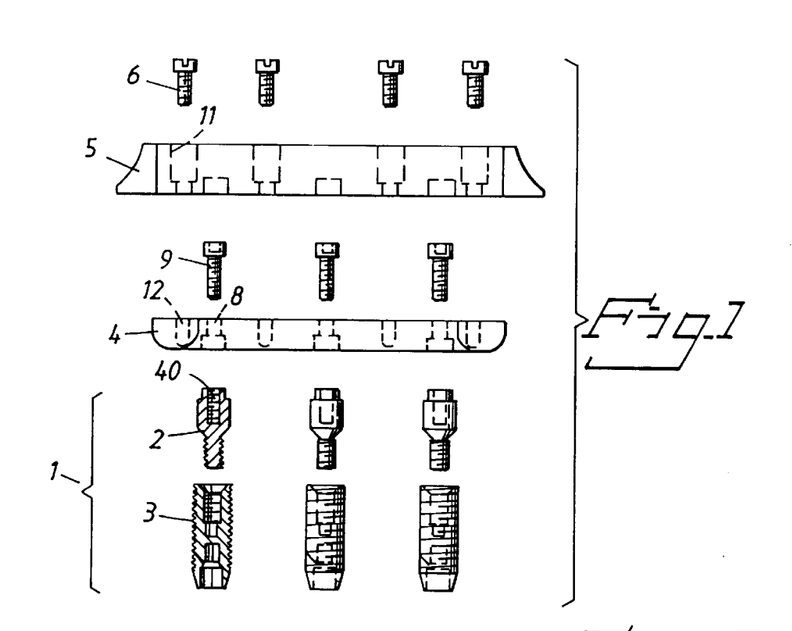
FIG. 1 is an exploded view of the components of a dental prosthesis bridge in accordance with the invention.
Figure 2:
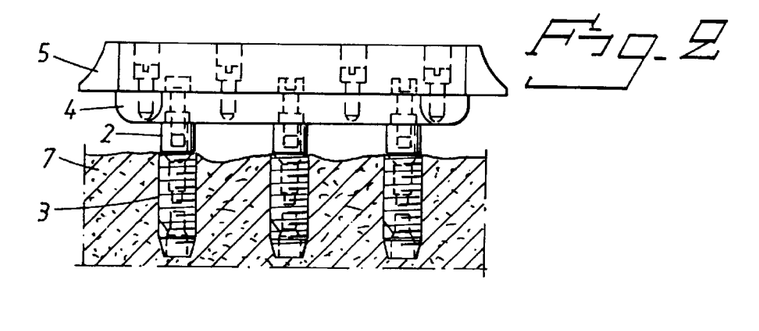
FIG. 2 shows the components in FIG. 1 when assembled.

FIGS. 1 and 2 illustrate the main components in a dental prosthesis system in accordance with the invention. These are shown most clearly by the exploded view in FIG. 1. A number of fixtures 1—three are shown in the example—are anchored in bone tissue 7 (see FIG. 2) in a person's lower jawbone. Each fixture contains an anchoring part 3 and a spacer part 2 that is attached to the anchoring part by means of, for example, a threaded joint. A bar 4 has three through-holes whose positions match the exposed ends of each fixture 1's spacer part 2 so that bar 4 can be fitted over these exposed ends. A screw 9 is passed through each hole 8 in bar 4 and screwed into place in a bore 40 in spacer part 2 to affix bar 4 to the three fixtures 1. On bar 4 there is a prosthesis bridge 5 that carries dental prostheses (not shown in FIGS. 1 and 2). This prosthesis bridge 5 is attached by means of four retainer screws 6 each of which is passed through its own hole in the prosthesis bridge and screwed in place in its own internally threaded bore 12 in the top of bar 4. FIG. 2 shows how the dental bridge is anchored in jawbone 7 by means of the described elements.

Figure 3:
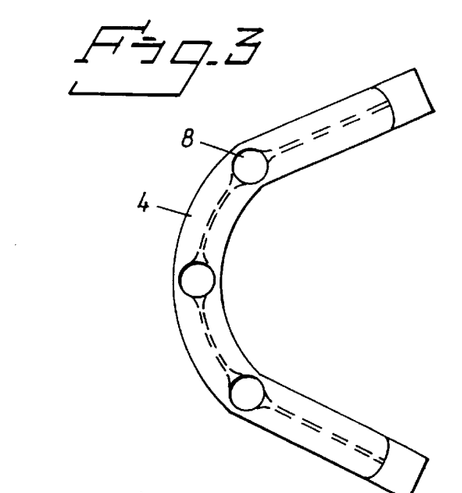
FIG. 3 is a top view of a part shown in FIG. 2.
Figure 4:
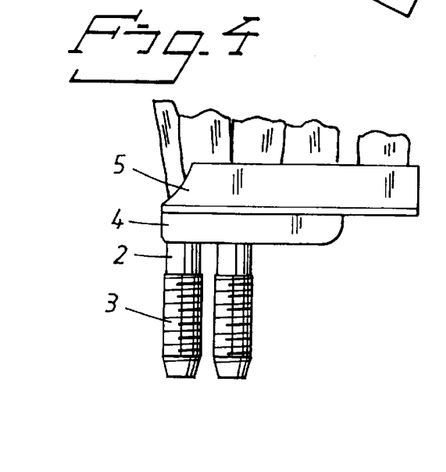
FIG. 4 is a side view of FIG. 2.

FIG. 3 is a bottom view of the bar 4 shown in FIG. 1, and it shows the positions of the three holes 8 that are fitted onto the three fixtures. FIG. 4 is a side view of the mounted dental prosthesis in FIG. 2 with the dental prostheses shown on dental prosthesis bridge 5.

In the system shown, all components that are included in the superstructure, i.e. bar 4, dental prosthesis bridge 5 and the retainer screws, are made of prefabricated elements. Having the screws and the dental prosthesis bridge supplied in this manner as standardized units does not pose a problem. The main difficulty is related to bar 4 which must be attached to a number of fixtures anchored in a unique person's jawbone. To make this possible, the fixtures must be anchored in the jawbone with mutually related positions that match the corresponding positions of bores 8, which comprise the attachment holes in standardized bar 4. The fixtures must also have precise mutual parallelism.

To achieve this, as mentioned previously by way of introduction, it is known to drill holes in jawbone 7 for fixtures using a drilling jig. However, with the drilling jigs encountered in dental prosthesis technology, it is impossible at present to provide drilled holes with sufficient precision to ensure that the fixtures anchored in them will exactly match a prefabricated bar having standardized positions for attachment holes 8. How drilling jigs can achieve such precision in accordance with the invention is explained below.

Figure 5:
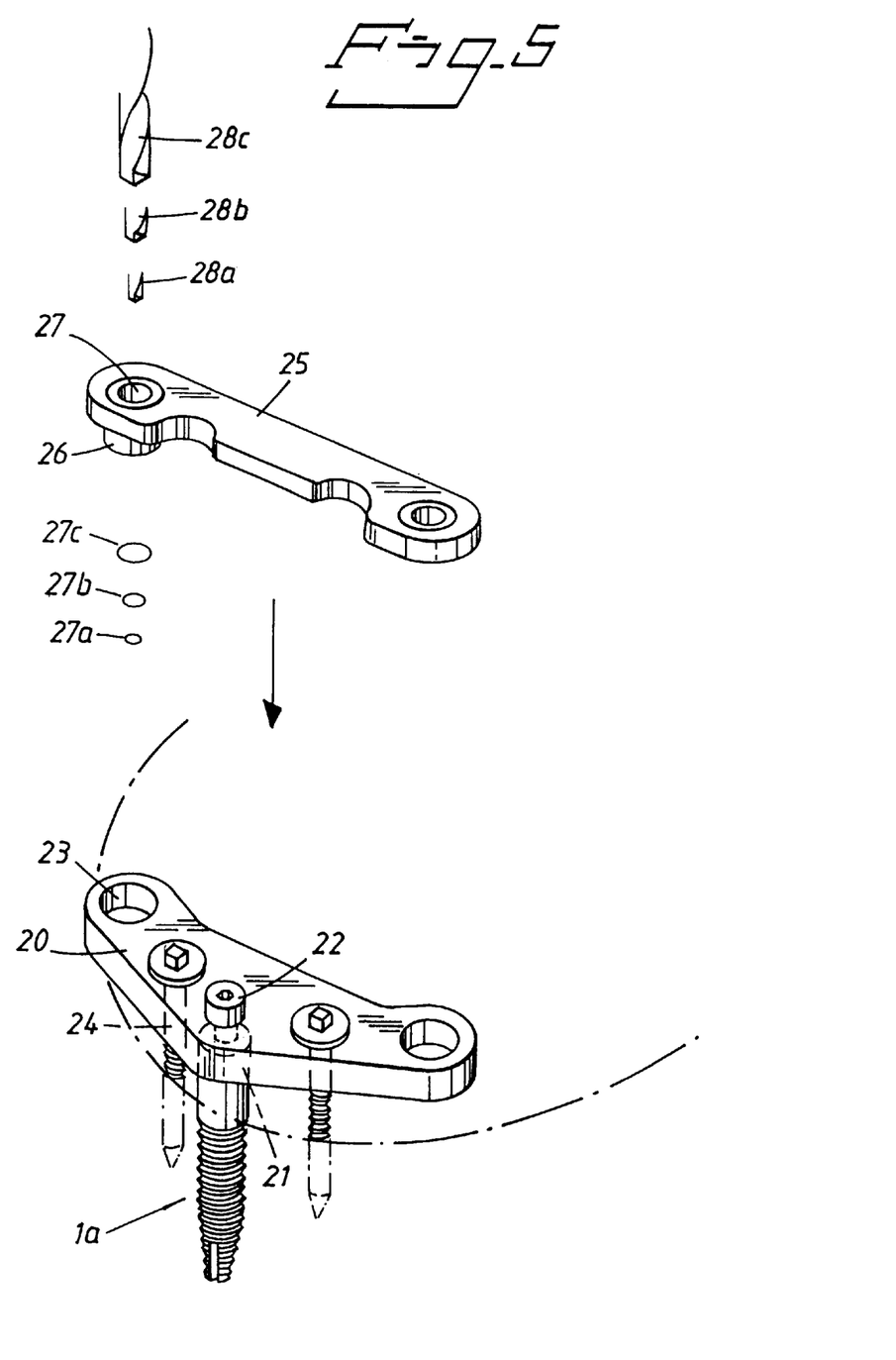
FIG. 5 is a perspective view of a drilling jig with associated elements in accordance with the invention.

FIG. 5 illustrates the application of the drilling jig to a person s jawbone in a way that will ensure the desired precision. As a first step, a hole is drilled for a first fixture located at the centre, and it serves as a reference device for drilling jig 20. Drilling jig 20 is provided with a centre-located through hole 21 which serves to align drilling jig 20 on centre-located fixture 1a. By means of retainer screw 22, which is of the same type as retainer screws 9 that are used to screw bar 4 in place on the fixtures, drilling jig 20 is now screwed firmly to reference fixture 1a, whereby drilling jig 20 assumes a well defined position. Drilling jig 20 is secured in this position by means of support screws 24 which are arranged on each side of reference fixture 1a and which are screwed through holes in the drilling jig into the person' jawbone. Drilling jig 20 has two through holes 23 at its outer ends. These serve as guides for drilling the holes needed for the two other fixtures.

Here, a set of setting sleeves 25 (only one of which is shown in the figure) which serves as a set of drill-guiding inserts is used, and each of these setting sleeves has two cylindrical projections 26 that slip very precisely into drilling jig holes 23 when setting sleeve 25 is placed on the top of drilling jig 20. Each sleeve 25 has a pair of through holes 27 that are coaxial with the cylindrical projections and which guide the drill-bits directly. Holes drilled in the jawbone are made in three stages. First, a setting sleeve with a relatively small hole 27a that is about 2 mm in diameter is used. Using this sleeve, a correspondingly fine drill bit 28a is used to drill into the jawbone. Thereafter, drilling jig 27 is replaced with a similar one, but having holes 27b of somewhat larger diameter, about 3 mm, and they are used for drilling with a second drill bit 28b of corresponding size. In the third stage, a drilling jig with holes 27c having a diameter of about 4 mm is used for final drilling of the fixture holes in the jawbone, and a correspondingly large drill bit 28c is used for this.

The drilled holes used for the two lateral fixtures are positioned very precisely thanks to drilling jig 20's well-defined position on the patient's jawbone. This was achieved by means of centre fixture 1a which serves as a reference and was the first fixture applied, by means of guide holes 23 which were positioned accurately with reference to centre fixture 1a and by means of the three setting sleeves 27. Moreover, holes 23 and the corresponding projections 26 and also holes 27a–c are long enough axially to ensure, together with the minimal clearance between holes 23 and projections 26 and also between holes 27a–c and drill bits 28a–c, that the three fixture holes in the jawbone will be parallel.

When this is done, the two lateral fixtures are anchored in the holes thus made. This is illustrated in the exploded drawings in FIGS. 6 and 7 which show the fixtures after they have been anchored in the jawbone. The same drilling jig 20 that was used to make the holes is kept mounted and used to apply the fixtures. A fourth sleeve 30, which serves as a fixture-guiding insert with cylindrical projections 31 that correspond to holes 23 in the drilling jig, is fitted into drilling jig 23. The fixture-guiding sleeve has holes 32 passing through the projections and arranged in the same way as on the drill-guiding sleeves. Each hole 32 in the fixture-guiding sleeve has a diameter adapted to accept, with an exact fit, an aligning element 33. This aligning element has a through hole 34 for a fixture-mounting screw 38. At bottom, the aligning element is provided with a hexagonal recess 35 that is somewhat wider than the through hole, and a bore 36 that is shallower than the recess and somewhat wider yet. The width and length of recess 35 is adapted to a hexagonal neck 42 on the upper end of fixture 16's spacer part 2b and the second bore 36 has a diameter that corresponds to the external shell surface 41 on spacer part 26.

Figure 6:
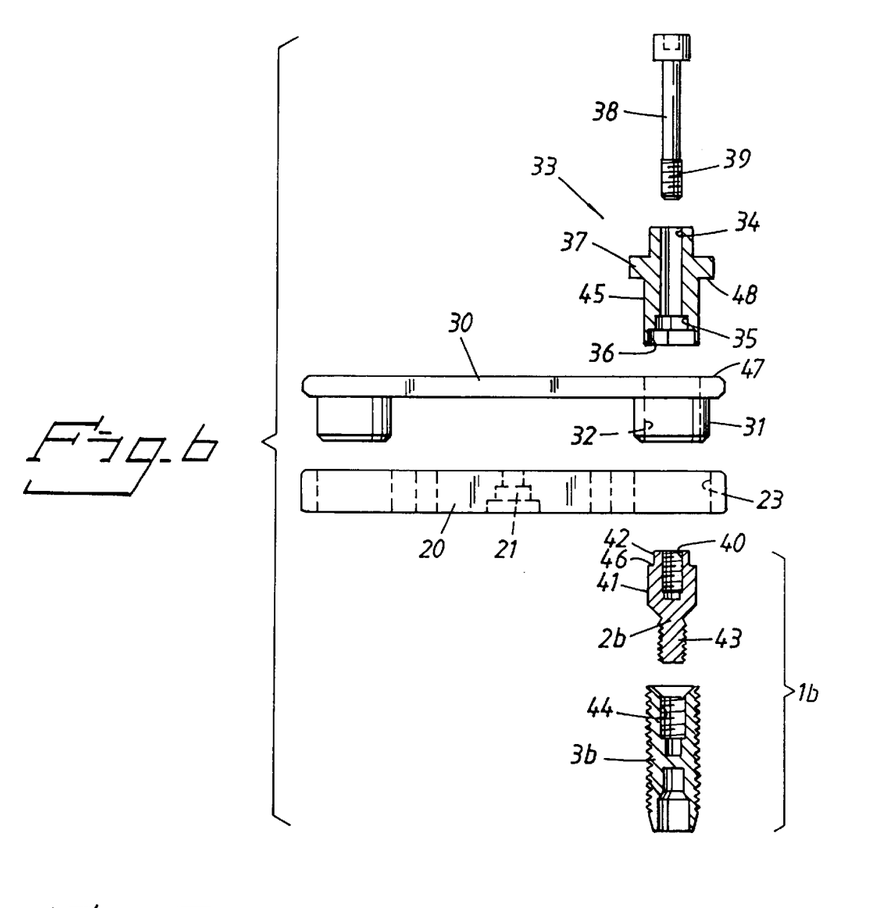
FIG. 6 is an exploded view of components used when mounting a superstructure in accordance with the invention.
Figure 7:
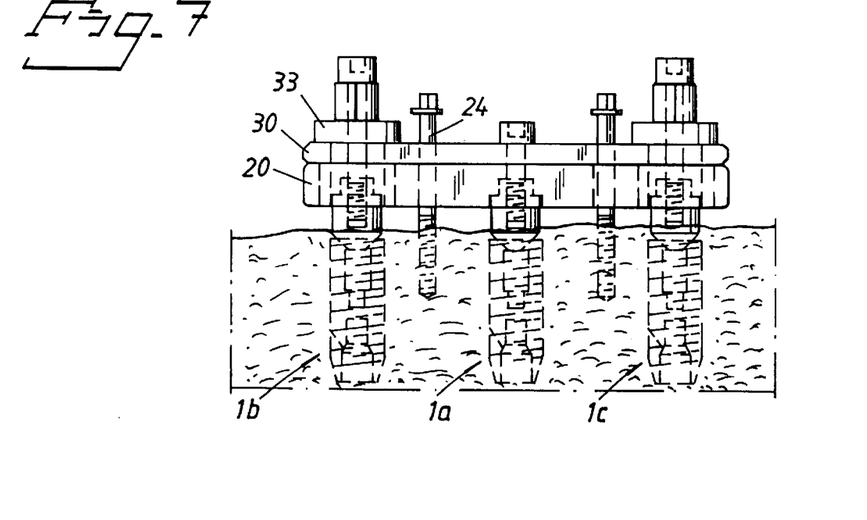
FIG. 7 shows the components in FIG. 6 when assembled.

Aligning element 33 us also provided with a radial flange 37 arranged so that, when mounted, it will contact setting sleeve 30's top side so as to provide a reference in the vertical direction.

Mounting screw 38, at its lower end, is provided with threads 39 that engage an internally threaded bore 40 in fixture 16's spacer element.

During mounting, fixture 1b 's anchoring part 36 and spacer part 26 are joined to form a single unit by screwing threaded part 43 of spacer part 2b into a bore having a mating internal thread in fixture 1b 's anchoring part 3b. Moreover, mounting screw 38 is passed through hole 34 in aligning element 33 and screwed into bore 40 in the top side of spacer part 2b so that bores 35, 36 in the aligning element surround the corresponding parts 42, 41 of spacer element 2b.

Mounting screw 38 and aligning element 33 as well as fixture 16's spacer part 2b and anchoring part 3b are thus passed as a single unit through hole 32 in sleeve 30, wherewith aligning element 33's external shell surface 45 fits hole 32 in sleeve 30 and is guided by it. Thereafter, mounting screw 38 is tightened. Since it is already tightened all the way to the bottom of spacer part 2b 's bore 40 and since spacer part 2b is screwed all the way into anchoring part 3b, the tightening of mounting screw 38 causes fixture 1b to be screwed into the hole drilled in the jawbone. Fixture 1b 's lower end is thus, in a known manner, designed to be self-tapping, and it is screwed down and anchored in the drilled hole. Screwing-in continues until aligning element 33's flange 37 comes into contact with sleeve 30's top side 47 which defines the correct screwing-in depth. This is shown most plainly in FIG. 7.

Figure 8:
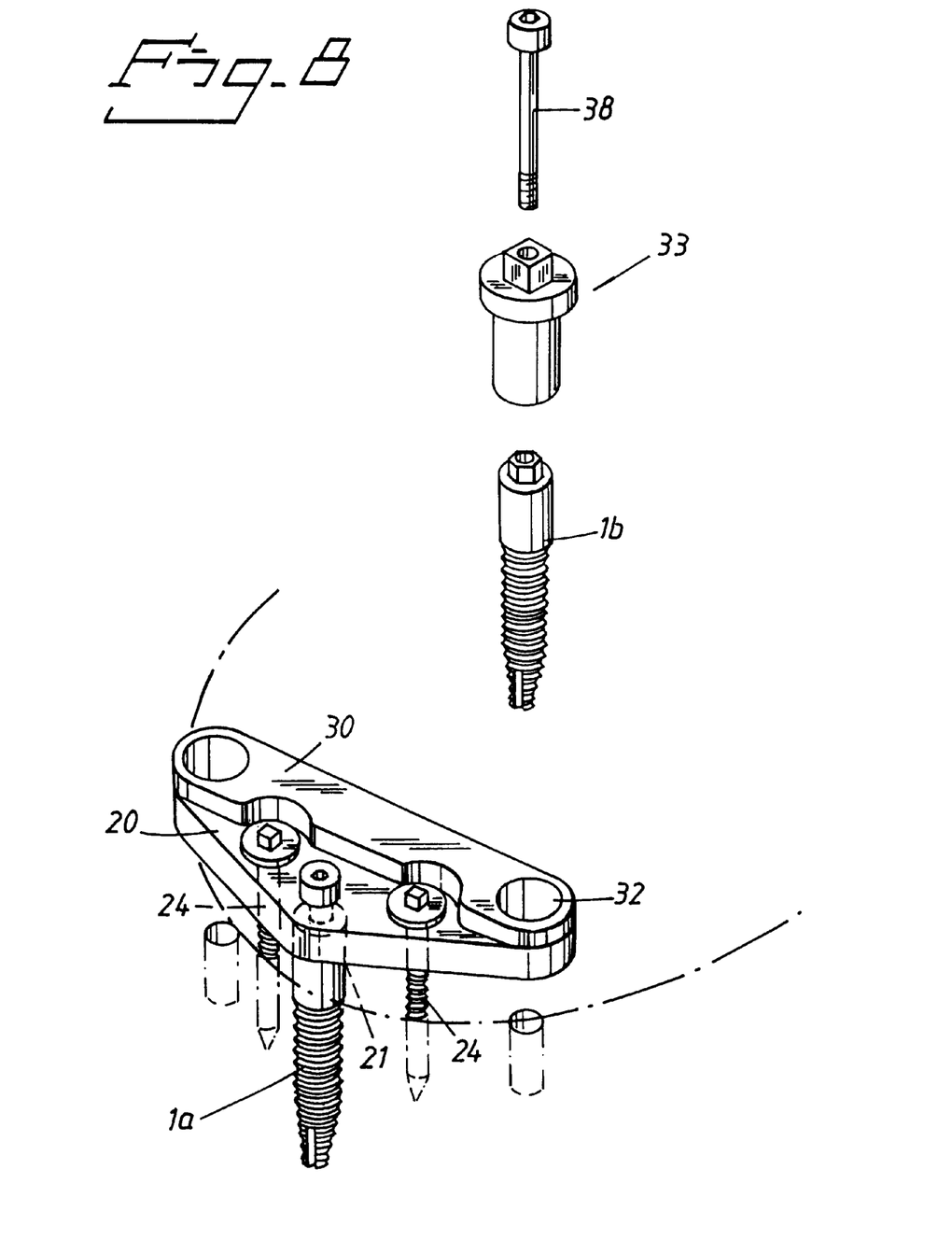
FIG. 8 is a perspective view of the components in FIG. 6.

FIG. 8 presents a perspective view of fixture mounting. When the lateral fixtures have also been anchored in this manner, all elements used for mounting are removed, i.e. mounting screw 38, aligning element 33, sleeve 30, drilling jig 20 and support screws 24.

Immediately thereafter, bar 4 shown in FIGS. 1–4 can be screwed firmly in place on the fixtures in the way set forth in the descriptions of these figures. After a healing-in time of about eight days, the dental bridge can be attached to the bar. During the waiting period, it may be advisable to attach a soft bar to bar 4 to protect it from chafing.

In spite of the accurate positioning of fixtures so that they will acquire positions and directions compatible with the fastening devices on the bridge base, there may be risk for some remaining inadequacy, particularly with regard to the mutual alignment directions of the fixtures. It is difficult to achieve complete mutual parallelism among the fixtures. This problem is described in greater detail in Swedish patent application No. 9602555-6, entitled "Fixtures, prosthesis anchoring arrangement and prosthesis", which is herewith referred to.

Figure 9:
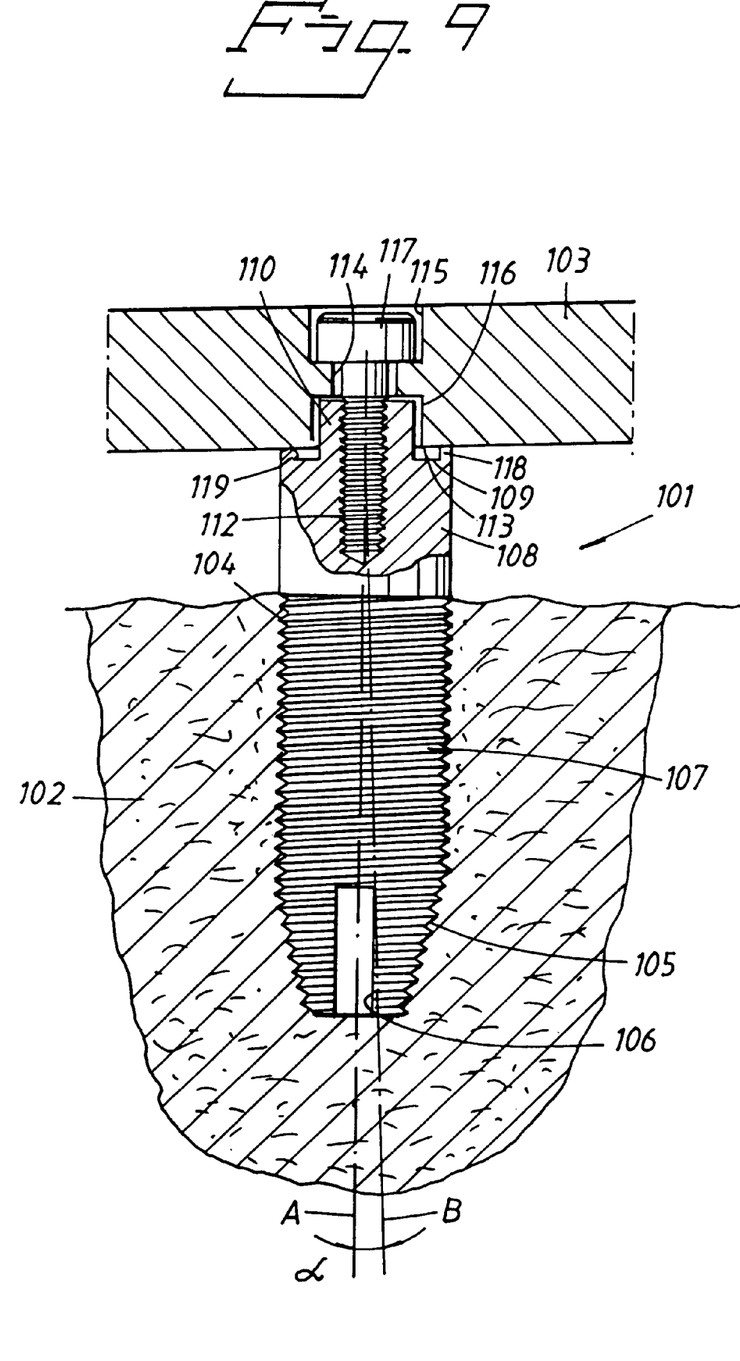
FIG. 9 is a partially sectioned side view of a fixture in accordance with a preferred embodiment of the invention.

To solve the problem caused by misalignment between a fixture's supporting surface and the corresponding bearing surface on the superstructure, a deformation device has been provided on the supporting surface of the fixture. One embodiment of this is illustrated in FIG. 9 which shows fixture 101 with its anchoring end anchored in a person's lower jawbone 102. At the upper end of fixture 101, its attachment comprises a bar 103 arranged so that it can carry a dental prosthesis bridge (not shown) that is attached to it.

Fixture 101's anchoring part 107 is designed in the conventional way with a threaded part 104 which, at its end, has a conic part 105 provided with slots 106. Anchoring part 107, which is made of titanium, is screwed self-tappingly into a pre-drilled hole in jawbone 102. The upper end of the fixture, which is its fastening end, comprises a spacer part 108 that can be integrated with anchoring part 107 to form a single piece or can be, as is more common, a separate unit that is screwed into a bore provided with internal threads (not shown in FIG. 9) in anchoring part 107.

The fastening end is provided with an attachment unit that engages another fastening unit adapted to it on bar 103, whereupon the two are fastened together. The fastening end's attachment unit contains a supporting surface 109 which is arranged perpendicularly to the fixture's longitudinal axis A. Said attachment unit also contains an axially aligned projection 110 that extends out from supporting surface 109, said projection having a hexagonal outer profile, and an internally-threaded bore 112 in the fixture. Bore 112 is axially aligned relative to the top of the projection. Bar 103's corresponding attachment unit includes a section of its bottom surface that comprises bearing surface 113, a through-going bore 114, a cylindrical countersink 115 at the upper end of the bore, a hexagonal countersink 116 at the lower end of the bore and a retainer screw 117.

Bar 103 defines a direction that is dependent on the direction of a first (not shown) fixture. An effort is made to see that this direction's normal alignment B will correspond to the shown direction of fixture 101. Such is not the case in the figure. Instead, there is a deviation of α° between them. A corresponding angular deviation also occurs between supporting surface 109 and bearing surface 113.

The fixture's bearing surface 109 is provided with a deformation device in the form of a flange 118 that is arranged at the periphery of bearing surface 109 and extends axially out from it. The flange is relatively thin, about 0.05 mm, and has a height of about 0.15 mm. When fixture 101 is pulled firmly onto bar 103 by tightening screw 117, the part of the fixture's supporting surface that consists of the flange will come into direct contact with bar 103's bearing surface 113. Since the surfaces are not parallel, the initial contact is made at a single point on flange 118. Continued tightening of the screw deforms flange 118 plastically at this location, and when the screw is further tightened the deformation extends throughout more and more of flange 118. At the left side of the figure, flange 119 is shown deformed in this manner. The deformed flange will therewith acquire an end surface that is parallel with bar 103's bearing surface 113 and contact it throughout it entire extent. As a result, angular deviation α has been compensated for in such a way that there is good contact between fixture 101 and bar 103, and so that no strains develop in jawbone 102. Instead of the flange, a plastically deformable ring-shaped washer can be put on the fixture's supporting surface.

What is claimed is:

1. A dental prosthesis system comprising:
   a superstructure provided with a first fastening device;
   a drilling jig; and
   a plurality of fixtures that can be implanted in a person's jawbone, each fixture including:
      an anchorage end arranged for anchoring in a jawbone; and
      a fastening end arranged for fastening said superstructure at each fixture;
   wherein at least one part of each fixture is substantially rotation-symmetrical and defines the center axis of said fixture;
   wherein said drilling jig comprises a fixed plate arranged to impart to said fixtures pre-determined mutual positions and impart to the center axes of said fixture pre-determined directions relative to each other, the drilling jig being provided with at least one guiding hole having a fixed position in the drilling jig and being arranged for guiding a drilling bit to make an anchorage hold in a person's jawbone; and
   wherein said superstructure includes prefabricated elements that incorporate said first fastening device and is adapted for attachment to said fixtures at said pre-determined mutual positions and in said mutual center axis directions; and
   wherein the system also contains a reference element attachable to a person's jawbone, said reference element being arranged to co-operate with said drilling jig by engagement therewith to position said drilling jig in a pre-determined position.

2. Dental prosthesis system in accordance with claim 1, wherein said reference element is a first fixture of said number of fixtures.

3. Dental prosthesis system in accordance with claim 1, further comprising at least one drill-guiding insert that can be fitted into each said guiding hole of said drilling jig.

4. Dental prosthesis system in accordance with claim 1, further comprising a fixture-guiding insert that can be fitted into each said guiding hole of said drilling jig, which fixture-guiding insert includes at least one fixture-guiding hole for guiding implanting of a fixture.

5. Dental prosthesis system in accordance with claim 4, further comprising fixture-aligning device arranged to be inserted in each said fixture-guiding hole and arranged so that with regard to direction and depth the fixture is guided by said fixture-guiding insert.

6. Dental prosthesis system in accordance with claim 1, wherein said directions are parallel.

7. Dental prosthesis system in accordance with claim 1, wherein one of the said directions defines an x-y plane perpendicular to said direction and for which said pre-determined mutual positions are pre-determined in said x-y plane.

8. Dental prosthesis system in accordance with claim 1, wherein the plurality of fixtures comprises three fixtures.

9. Dental prosthesis system in accordance with claim 1, wherein said superstructure contains holes whose positions and directions correspond to said first fastening fixture positions and directions.

10. Dental prosthesis system in accordance with claim 1, wherein said superstructure contains a bar equipped with said first fastening device and a dental prosthesis bridge having a second fastening device for fastening said bridge to said bar.

11. Dental prosthesis system in accordance with claim 1, wherein said superstructure contains a dental prosthesis bridge provided with said first attachment device.

12. Dental prosthesis system in accordance with claim 1, wherein said fixtures are, at least in part, made of a material containing titanium.

13. Dental prosthesis system in accordance with claim 1, wherein said fixtures contain parts having a surface texture containing micro-porosities on the order of magnitude of 10–1000 nm, preferably 10–300 nm, thereby enhancing osseintegration with bone tissue in the jawbone.

14. Dental prosthesis system in accordance with claim 1, wherein at least one of said fixtures contains a supporting surface and said first fastening device contains a bearing surface compatible with each supporting surface where said bearing surface is arranged so that said bearing surface will be supported against the corresponding supporting surface after attachment.

15. Dental prosthesis system in accordance with claim 14, further comprising a plastic deformation device arranged so that when it is attached it will be located between said bearing surface and said corresponding supporting surface for at least one of said fixtures.

16. Dental prosthesis system in accordance with claim 15, wherein said deformation device contains a cylindrical flange projecting out from at least one of said bearing surfaces and said supporting surfaces.

17. Dental prosthesis system in accordance with claim 15, wherein said deformation device contains a plastic, separate body.

18. Dental prosthesis system in accordance with claim 15, wherein said deformation device is deformable in the center-axis-defined axial direction of the associated fixture.

* * * * *